United States Patent
Dickopp et al.

(10) Patent No.: US 6,869,392 B2
(45) Date of Patent: Mar. 22, 2005

(54) DISPOSABLE IMPLEMENT INSERTED INTO AN ENDOSCOPE

(75) Inventors: Jorg Dickopp, Reinbeck (DE); Henning Wedler, Hamburg (DE)

(73) Assignee: Olympus Winter & IBE GmbH, Hamburg (DE)

( * ) Notice: Subject to any disclaimer, the term of this patent is extended or adjusted under 35 U.S.C. 154(b) by 0 days.

(21) Appl. No.: 10/412,167

(22) Filed: Apr. 11, 2003

(65) Prior Publication Data

US 2003/0199735 A1 Oct. 23, 2003

(30) Foreign Application Priority Data

Apr. 17, 2002 (DE) .......................................... 102 16 928

(51) Int. Cl.⁷ ................................................. A61B 1/00
(52) U.S. Cl. ...................................... 600/104; 600/133
(58) Field of Search ................................ 600/104, 106, 600/153, 133, 155

(56) References Cited

U.S. PATENT DOCUMENTS

| 5,368,606 A | | 11/1994 | Marlow et al. |
| 5,447,265 A | * | 9/1995 | Vidal et al. ............... 227/176.1 |
| 5,569,163 A | | 10/1996 | Francis et al. |

FOREIGN PATENT DOCUMENTS

| WO | WO9837819 | * | 9/1998 | ........... A61B/17/32 |

* cited by examiner

*Primary Examiner*—Beverly M. Flanagan
(74) *Attorney, Agent, or Firm*—Rankin, Hill, Porter & Clark LLP

(57) ABSTRACT

A disposable implement insertable into an endoscope and comprising at least one zone matched to the shape of the endoscope. The at least one zone is designed to be permanently deformed on account of having been used a first time by the inevitable mechanical, thermal and/or chemical treatment it undergoes in the endoscope, and before renewed use in the endoscope. Deformation of the at least one zone eliminates shape-matching of the zone to the endoscope, and is readily visually apparent to a user.

10 Claims, 2 Drawing Sheets

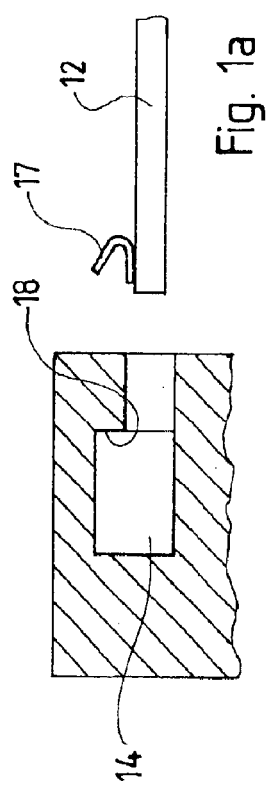
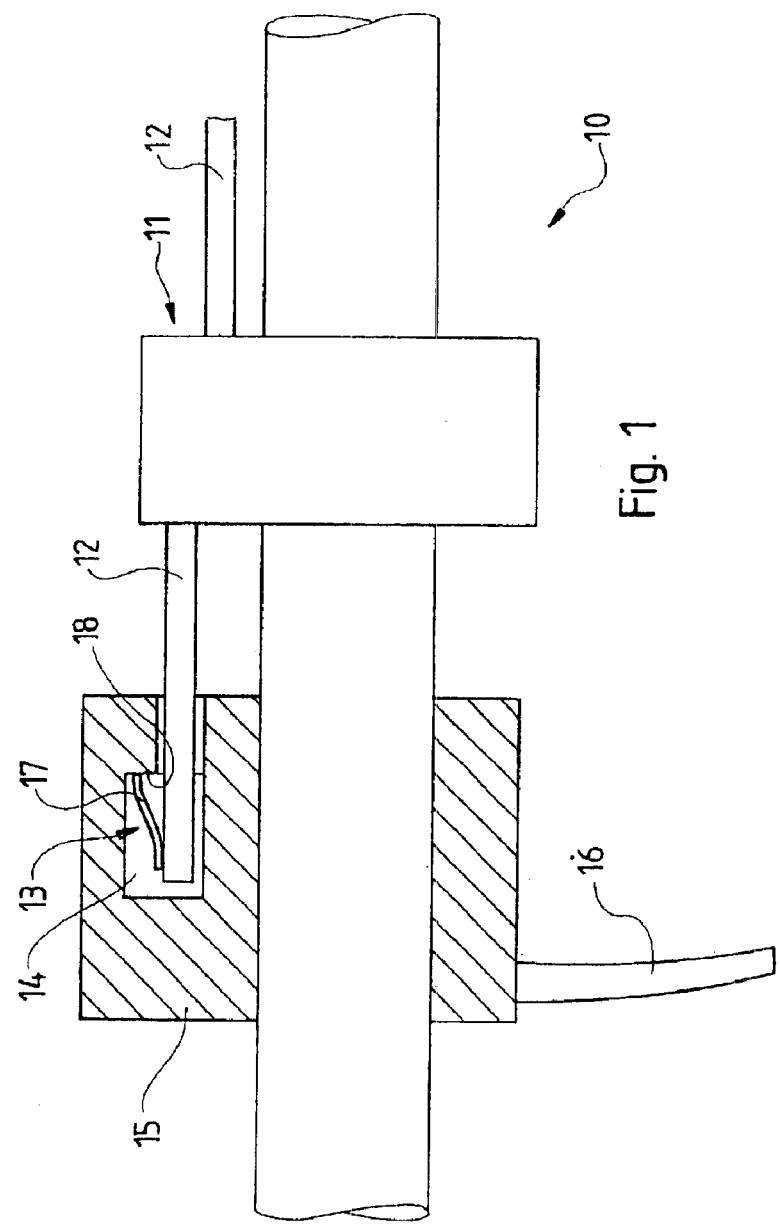

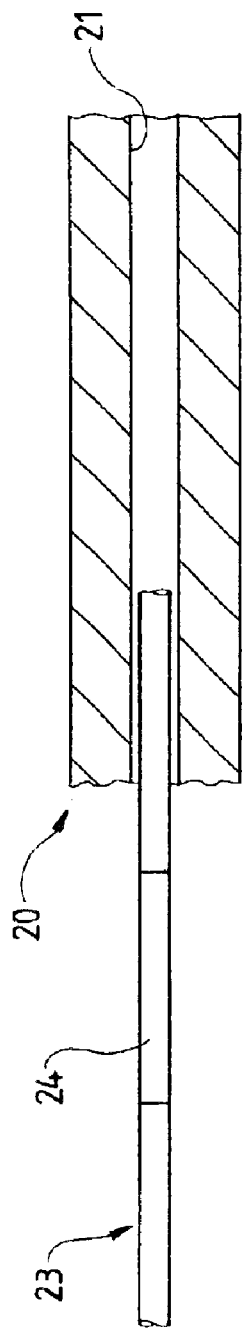
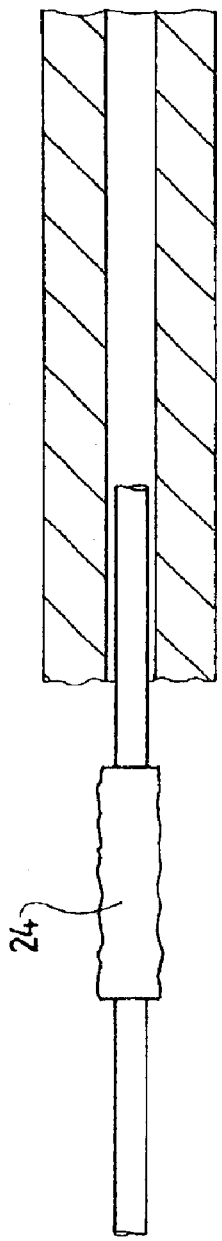
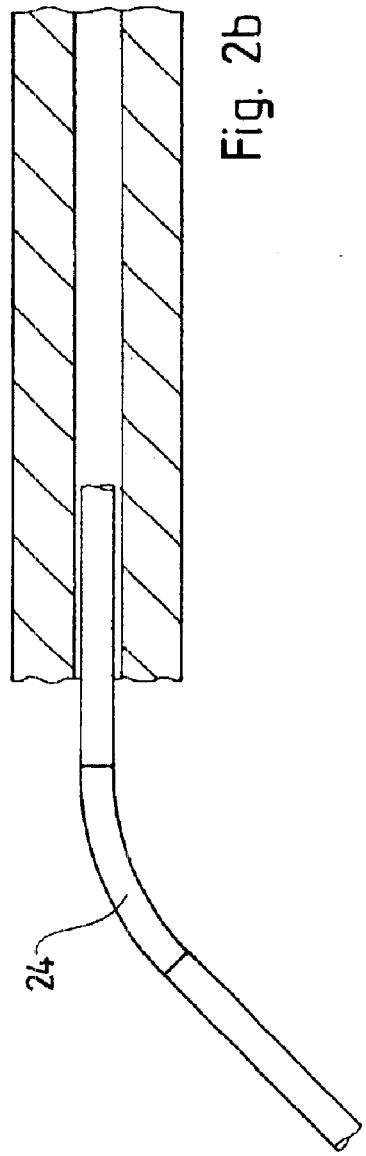

DISPOSABLE IMPLEMENT INSERTED INTO AN ENDOSCOPE

BACKGROUND OF THE INVENTION

1. Field of the Invention

The present invention is directed toward endoscopic implements and, more particularly, toward single-use disposable implements that designed for use in endoscopes. Such implements include electrodes, knife blades, milling elements, drill bits, and tongs, among many others.

2. Description of Related Art

Disposable implements may be inserted in different ways into the endoscopes. Generally, disposable implements are geometrically adapted or shape-matched to the endoscope, or they conform, at least in part, to the shape or geometry of the endoscope.

Illustratively, the endoscopes may exhibit an operational duct permitting insertion of the disposable implements, which conventionally include an elongated stem. The conventional disposable implement's stem, for instance, includes at least one geometrically adapted or shape-matched zone, which is fitted to the operational duct's diameter so as to allow insertion without vexatious play. In general the stem is matched to the shape of the duct over its full length.

The disposable implements may be further geometrically adapted or shaped, for instance in a connection zone. For example, it is known to use a spring element at the proximal end of electrode supports, the spring element after being inserted into the slider resiliently engaging the rear of an edge thereof and locking the electrode support in the slider. Conventionally, the implement or the slider is fitted with unlocking means to permit removal of the slider.

For the sake of patient safety, disposable implements should only be used once and then be destroyed.

SUMMARY OF THE INVENTION

The present invention is directed toward an improved disposable implement for use in an endoscope, wherein the implement precludes erroneous re-using thereof.

In accordance with the present invention, at least one geometrically adapted or shape-matched zone of the implement is made to be irreversibly deformable. The zone is selected so as to be deformed by mechanical, thermal, and/or chemical treatment perforce required before the implement might be used again in such a way that the geometric adaptation or shape-matching between the disposable implement and the endoscope is eliminated.

In accordance with the present invention, the "perforce required treatment" includes comprises all actions required in conventional medical procedures to prepare a used implement for renewed use on another patient. In general, such an action requires separating the disposable implement from the endoscope. Among other mandatory actions, this step must be followed by cleaning and sterilization of the endoscope and the implement.

For instance, a disposable implement of the present invention may be fitted with a geometrically or shape-matched stem zone that undergoes a change in diameter in the course of thermal sterilization such that the stem can no longer be inserted into the host endoscope operational duct or passageway, or else can only be inserted after overcoming substantially more resistance.

Additionally, an element used to lock a disposable implement in the endoscope will also be bent or otherwise deformed when the disposable implement is withdrawn from the endoscope, whereby renewed locking shall be impossible or only possible with substantial difficulty. Illustratively, as regards the initially cited locking of an electrode support, a spring element might be mounted on this support and the means present conventionally at the slider no longer would be able to unlock the element, or the release means might be omitted.

In further accordance with the present invention, deformation of the geometrically or shape-matching zone is clearly visible. Conceivably, a clearly visible change in diameter of the geometric adaptation may taken place subsequent, for instance, to swelling due to exposure to superheated steam, or a straight disposable implement shall be bent, etc. It is an easy matter for the expert to select appropriate materials that, for instance, in the presence of superheated steam or during dry sterilization undergo the desired deformation.

In both instances reinsertion of the disposable implement into an endoscope at least was made difficult. Moreover, it is indicated in a clearly visible manner that a disposable implement not intended for reuse has been sterilized.

In further accordance with the present invention, the implements are designed such that their basic operations or functions remain feasible without jeopardizing safety even after the geometrically adapted zone was deformed. In other words, the deformation of the geometrically matched zone does not affect essential procedures or functions and, in particular, parts of the disposable implement are not loosened and do not drop off. The changes that do occur shall only assure that a surgeon, at the latest when reinserting the implement into the endoscope, shall become aware, on account of the increased resistance or difficulties of locking the implement being inserted into the endoscope, that such a disposable implement is about to be used again. If the implement allows being inserted/locked a second time, then its operability shall be assured also during this second surgery.

BRIEF DESCRIPTION OF THE DRAWINGS

These and further features of the invention will be apparent with reference to the following description and drawings, wherein:

FIG. 1 shows a zone whereby an electrode support is locked to an endoscope slider;

FIG. 1a shows a corresponding zone of the electrode support after it has been retracted from the slider;

FIG. 2 shows a disposable implement insertable into an endoscope's operational duct during a first use;

FIG. 2a shows an embodiment of an implement of FIG. 2 subsequent to deformation; and, FIG. 2b shows another embodiment of an implement of FIG. 2 subsequent to deformation.

DETAILED DESCRIPTION OF THE PREFERRED EMBODIMENTS

FIG. 1 is a partial view of a resectoscope 10 with apposed electrode support 11. An electrode 12 is received in the electrode support 11 and is affixed by means of a proximal, geometrically-adapted or shape-matched zone 13 in a clearance 14 of a slider 15, which displaceably rests on the resectoscope 10. The slider 15 may be displaced by means of a grip 16 in the longitudinal resectoscope direction.

The geometrically adapted or shape-matched zone 13 of the electrode 12 is fitted with a resilient element 17 that, subsequenty to the electrode's 12 insertion, elastically spreads out by its proximal end into the clearance 14 in order to lock against an edge 18. When the electrode 12 is pulled out of the clearance 14, the resilient element 17 is bent into the opposite direction and retains this bent condition, as shown in FIG. 1a. FIG. 1a further shows that repeated insertion of the electrode 12 into the clearance 14 will be difficult. At a minimum the resilient element would have to be bent back into its original direction or orientation. Upon this attempted displacement, the surgeon would notice that the implement has already been used.

FIG. 2 shows another embodiment of the present invention, and illustrates an arbitrary endoscope 20 defining an operational duct 21.

In the state shown in FIG. 2, a stem 23 of a disposable implement is being inserted into the operational duct 21 of the endoscope 20. The implement has a zone 24 matching the shape of the operational duct 21.

The zone 24 is made of a special material that, for example, shall swell upon being exposed to heat. Alternatively, the zone 24 may change in some other way. FIG. 2a illustrates one possible state of the zone 24, for instance, subsequent to a sterilizing procedure. It is clear that the zone 24 has swollen so much that it can no longer be inserted, or only with substantial difficulty, into the operational duct 21.

FIG. 2b shows another embodiment wherein the zone 24 exhibits a bend, for instance following a sterilizing procedure, so that re-insertion again will be difficult.

The above shown embodiments are intended to represent the invention merely in an exemplary manner. Other designs are also feasible whereby, for instance, a template or a passageway of given peripheral or cross-sectional shape is predetermined to receive the disposable implement.

Due to the application of heat or another treatment, the result of a first use of said implement is that a correspondingly geometrically adapted or shape-matched zone of the disposable implement shall be changed such that the zone can no longer traverse the template or the passageway.

As shown above, most diverse designs are available to implement the present invention.

The expression "geometrically adapted or shape-matched zone" applies widely. It is meant to cover any disposable implement zone which may be deformed on account of a treatment, for instance when retracting the disposable implement from the endoscope or when mandatorily sterilizing the implement before using it again, in such a way that new insertion or locking of the disposable implement into or to the endoscope must entail problems.

If this principle also should visually observable, then zones may be provided in the disposable implement that, besides undergoing a change in dimensions, also shall undergo, for instance, a change in color. Moreover the deformation of the disposable implement might be so substantial—for instance in the form of kinking, sharp swelling, etc.—that it shall be clear very soon to the surgeon (that is before an attempt is made to repeat inserting into the endoscope) that the attempt is made to reuse a disposable implement.

What is claimed is:

1. A disposable implement for insertion into an endoscope and comprising at least one zone matched to a shape of the endoscope, said implement being initially inserted into the endoscope with a first force prior to a first use of said implement in the endoscope and wherein the zone (17, 24) is adapted to become permanently deformed subsequent to the first use and before a second use of the implement in the endoscope (10, 20,), said implement being permanently deformed by a treatment selected from the group consisting of mechanical, thermal and chemical treatments, such that shape matching of the implement to the endoscope is permanently eliminated, said implement, following said treatment and despite said permanent deformation, may be reinserted into the endoscope with a second force and used within said endoscope, wherein said second force is substantially greater than said first force and thereby alerts a user to the second use of the implement in the endoscope.

2. The disposable implement as claimed in claim 1, wherein deformation of the implement results in a clearly visible change in said at least one zone (13, 24).

3. The disposable implement as claimed in claim 1, wherein deformation of the zone (24) is accomplished by a thermal treatment.

4. The disposable implement as claimed in claim 1, wherein the deformation of the zone (13) takes place while the disposable implement (12) is being removed from the endoscope (10).

5. The disposable implement as claimed in claim 1, wherein, after deformation of the zone and re-insertion of the implement into the endoscope, basic functions of the implement are preserved in a manner safe for the patient.

6. The disposable implement as claimed in claim 2, wherein deformation of the zone (24) is accomplished by a thermal treatment.

7. The disposable implement as claimed in claim 2, wherein the deformation of the zone (13) takes place while the disposable implement (12) is being removed from the endoscope (10).

8. The disposable implement as claimed in claim 2, wherein, after deformation of the zone and reinsertion of the implement into the endoscope, basic functions of the implement are preserved in a manner safe for the patient.

9. The disposable implement as claimed in claim 3, wherein, after deformation of the zone and reinsertion of the implement into the endoscope, basic functions of the implement are preserved in a manner safe for the patient.

10. The disposable implement as claimed in claim 4, wherein, after deformation of the zone and reinsertion of the implement into the endoscope, basic functions of the implement are preserved in a manner safe for the patient.

* * * * *